United States Patent [19]

Teetz

[11] Patent Number: 4,515,960
[45] Date of Patent: May 7, 1985

[54] SPIRO-2-AZA-ALKANE-3-CARBONITRILES, THEIR PREPARATION AND THEIR USE

[75] Inventor: Volker Teetz, Hofheim am Taunus, Fed. Rep. of Germany

[73] Assignee: Hoechst Aktiengesellschaft, Frankfurt am Main, Fed. Rep. of Germany

[21] Appl. No.: 494,983

[22] Filed: May 16, 1983

[30] Foreign Application Priority Data

May 17, 1982 [DE] Fed. Rep. of Germany ....... 3218540

[51] Int. Cl.³ .................. C07D 221/20; C07D 223/32; C07D 223/14; C07D 225/06
[52] U.S. Cl. ................................ 548/408; 260/239 B; 546/16; 564/455; 549/347; 549/373; 549/451
[58] Field of Search .......................... 548/408; 546/16; 260/239 B

[56] References Cited

U.S. PATENT DOCUMENTS 3,957,820  5/1976  Zondler ............................. 548/408

FOREIGN PATENT DOCUMENTS 2756360  6/1978  Fed. Rep. of Germany .
1598095  9/1981  United Kingdom .
1598096  9/1981  United Kingdom .

Primary Examiner—Mark L. Berch
Attorney, Agent, or Firm—Finnegan, Henderson, Farabow, Garrett & Dunner

[57] ABSTRACT

The invention provides compounds of the formula I

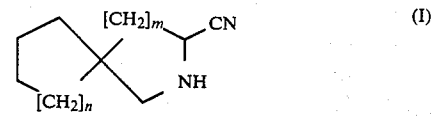

in which m is 1 to 3 and n is 1 to 4, a process for their preparation, and their use as intermediates for the manufacture of valuable medicaments, and starting products for the preparation of compounds of the formula I.

2 Claims, No Drawings

SPIRO-2-AZA-ALKANE-3-CARBONITRILES, THEIR PREPARATION AND THEIR USE

The invention provides compounds of the formula I

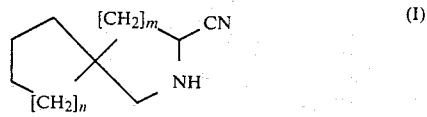 (I)

in which m is an integer of from 1 to 3 and n is an integer of from 1 to 4. Particularly preferred are compounds of the formula I, in which m is 1.

The invention provides furthermore a process for the preparation of compounds of the formula I, which comprises treating compounds of the formula II

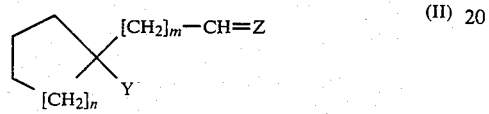 (II)

in which m and n are as defined above, Y is aminomethyl and Z is a protective oxo group which can be split off by acids and is inert to organo-metal reagents, (a) with acids and subsequently (b) with hydrogen cyanide or cyanides.

Preferred protective groups Z of oxo function are groups of the formula $(OR^1)_2$, in which $R^1$ is alkyl having from 1 to 6, preferably 1 to 4, carbon atoms, or the two radicals $R^1$ together are alkylene having from 2 to 5 carbon atoms. For the reaction of the preferred acetals of the formula II (Y=CH$_2$NH$_2$), dilute mineral acids such as hydrochloric or sulfuric acid, furthermore organic acids such as acetic, oxalic or tartaric acid have proved to be appropriate. The treatment of the protected compounds of the formula II (Y=CH$_2$NH$_2$) with strong acids, preferably hydrochloric acid, yields aldimine with simultaneous splitting-off of the protective group, and subsequently hydrogen cyanide is added onto the aldimine under conditions analogous to the Strecker synthesis.

It has been found that the reaction with hydrogen cyanide proceeds in a considerably improved manner and with high yields when it is carried out in a solution of acetic acid.

Alternatively to hydrogen cyanide, cyanides, preferably alkali metal and alkaline earth metal cyanides, are suitable.

The compounds of the formula II, in which m, n, Y and Z are as defined above, are obtained by metalating cycloalkane-carbonitriles of the formula IV

 (IV)

in which n is as defined above, in alpha-position and reacting them with a protected ω-haloaldehyde of the formula X—[CH$_2$]$_m$—CH=Z, in which m and Z are as defined above and X is bromine or chlorine (acetals being preferred), to give a compound of the formula II, in which m, n and Z are as defined above and Y is cyano. Subsequent reduction yields the aminomethyl compound of the formula II. The process as described starts from simple and easily obtainable preliminary products and gives yields of more than 80% in each step.

The alpha-metalation of the nitriles of the formula IV is carried out with known reagents; suitable are for example potassium amide in liquid ammonia, or lithium diethylamide in HMPT or preferably in hexane. A corresponding solution can be prepared according to known methods (see for example Houben-Weyl, Methoden der organischen Chemie). Suitable alkylation reagents are any aliphatic chlorine or bromine compounds of protected aldehydes, preferably acetals. The kind of acetal chosen is irrelevant for the reaction, so that for example dimethyl- or diethylacetals, cyclic acetals such as ethyleneacetal, or higher homologs may be used. The nitrile group is advantageously reduced by means of metallic sodium in alcohol. Catalytic reaction with Raney nickel is also possible; in this case, however, the reaction should be carried out in acetic anhydride in the presence of bases. The N-acetal derivatives of the compounds of formula II obtained can likewise be used in the subsequent reaction steps.

The invention relates furthermore to compounds of the formula II, in which Z, m and n are as defined above and Y is aminomethyl or cyano. Preferred are compounds of the formula II, in which m is 1, and especially those where Y is aminomethyl.

The invention provides furthermore a process for the preparation of compounds of the formula III

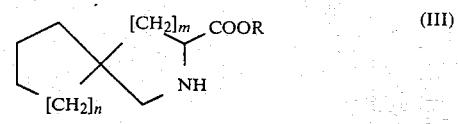 (III)

in which m and n are as defined above and R is hydrogen, alkyl having from 1 to 10 carbon atoms, aralkyl having from 7 to 9 carbon atoms, cycloalkyl having from 5 to 10 carbon atoms, alkylcycloalkyl or cycloalkylalkyl each having from 6 to 12 carbon atoms, by solvolysis of compounds of the formula I, in which m and n are as defined above, with a compound of the formula ROH, in which R is as defined above.

The nitrile of the formula I is saponified according to known methods. Especially suitable is the saponification with mineral acids such as for example 4N hydrochloric acid. The esters are prepared from the amino acids formed according to the usual methods of peptide chemistry. It has proved to be especially favorable to convert the aminonitriles directly to the esters with corresponding alcohols in an anhydrous medium in the presence of acidic catalysts (for example gaseous HCl), so that this process is preferred.

The compounds of the formula I are preferably used for the preparation of those compounds of the formula III, in which R is hydrogen, alkyl having from 1 to 10 carbon atoms, aralkyl having from 7 to 9 carbon atoms, especially benzyl and nitrobenzyl, or alkylcycloalkyl having from 6 to 10 carbon atoms; the radicals R optionally being chiral, such as menthyl.

The compounds of the formulae I and III are intermediates for the preparation of compounds of the formula V

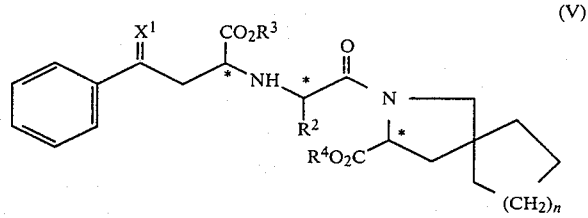

(V)

in which n is 1, 2, 3 or 4,

R² is alkyl or a natural amino acids HOOC—CH(NH₂)—R¹,

R³ is hydrogen, alkyl having from 1 to 6 carbon atoms or optionally nitrosubstituted aralkyl having from 7 to 9 carbon atoms, R⁴ is hydrogen, alkyl or cycloalkyl having from 1 to 10 carbon atoms or optionally nitrosubstituted aralkyl having from 7 to 9 carbon atoms, and X¹ represents 2 hydrogen atoms or 1 oxygen atom, and the physiologically tolerable salts thereof with acids or, in the case where R² and/or R³ are hydrogen, with bases.

In this formula V, the carbon atom in position 3 of the spirocycle and the carbon atoms of the chain labelled with an asterisk (*) may have an R or S configuration. Compounds the carbon atom in position 3 of the spirocycle and the carbon atoms of the chain labelled with an asterisk of which have an S configuration are preferred.

The process for preparing compounds of the formula V comprises condensing compounds of the formula VI

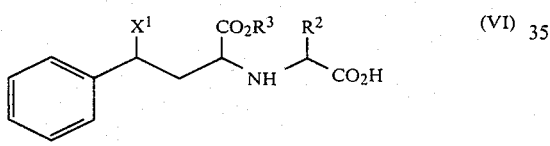

(VI)

in which R², R³ and X¹ are as defined above with compounds of the formula III, in which R and n are as defined above with the exception of R=hydrogen, and m is 1, subsequently splitting off optionally the radicals R³ and/or R⁴ by hydrogenolysis or with acids or bases, and optionally converting the compounds of the formula V obtained to their physiologically acceptable salts.

Condensation of the compounds of the formula VI with the esters of the formula III is preferably carried out according to known methods of peptide chemistry. Particularly appropriate are those methods which sufficiently protect from racemization, such as the DCC/HOBt method or the alkanephosphonic acid anhydride method described in U.S. Pat. No. 4,331,592.

Compounds of the formula V, in which at least one of the radicals R³ and R⁴ is hydrogen can be converted in known manner to the esters of the formula V in which R³ and R⁴ are as defined above with the exception of being hydrogen.

The compounds of the formula V have a long-lasting, intense hypotensive action. They are well absorbed after peroral administration and can be applied for combating hypertension of different genesis either alone or in combination with other hypotensive, vasodilative or diuretic compounds. Administration may be intravenously, subcutaneously or perorally; the latter being preferred at an individual dose of from 0.1 to 100 mg.

This dose may be increased in serious cases, because toxic effects have not been observed hitherto. On the other hand, the dose may be reduced, especially when diuretics are administered simultaneously. In case of intravenous or subcutaneous administration, the individual dose should be from 0.01 to 20 mg.

In animal tests, the following effects were obtained (the inhibition of the pressor response induced by 310 ng of angiotensin I was measured in rats):

| (a) i.v. administration (30 min. after administration) | | | | |
|---|---|---|---|---|
| Compound V R³ | n | X¹ | Dose | % Inhibition |
| $C_2H_5$; | 1; | $= H_2$ | 100 μg/kg | 95% |
| $C_2H_5$; | 2; | $= H_2$ | 100 μg/kg | 95% |
| $C_2H_5$: | 2; | $= O$ | 100 μg/kg | 95% |
| H; | 3; | $= H_2$ | 100 μg/kg | 95% |
| (b) i.d. administration (30 min. after administration) | | | | |
| R³ | n | X¹ | Dose | % Inhibition |
| $C_2H_5$ | 1; | $= H_2$ | 1 mg/kg | 85–95% |
| $C_2H_5$ | 2; | $= H_2$ | 0.1 mg | 60–70% |

The compounds of the formula V in which R⁴ is hydrogen are present as inner salts. In the case where both carboxyl groups are free, alkali metal, calcium, magnesium and zinc salts and salts with physiologically tolerable amines can be formed in addition. Furthermore, the free amino group can be converted to a salt by means of a mineral acid or organic acid.

The following examples illustrate the invention.

EXAMPLE 1

1-(Di-(ethyloxy)ethyl)-cyclohexane-carbonitrile 51.7 ml (0.5 mol) of anhydrous diethylamine are added dropwise to 312.5 ml (0.5 mol) of a 15% solution of n-butyl-lithium in hexane at −10° C. under an inert gas blanket. The batch is stirred for 10 minutes and then cooled to −70° C. Within 30 minutes, 54.6 g of cyclohexane-carbonitrile are added dropwise, after a further 30 minutes 98.5 g of bromoacetaldehyde-diethylacetal are added within 1 hour, and the batch is maintained for 24 hours at low temperature. Subsequently, it is warmed to room temperature, given onto 100 g of ice, extracted twice with 500 ml of ethyl acetate, the organic phase is dried over sodium sulfate, concentrated in vacuo, and the residue is subjected to vacuum distillation.

Yield: 90 g (abt. 80% of th.) b.p. 78°–79° C. at 8 mm Hg.

EXAMPLE 2

1-Aminomethyl-1-(di(ethoxy)ethyl)-cyclohexane 90 g of di-(ethyloxy)ethyl-cyclohexane-carbonitrile are dissolved in 1 l of ethanol, and 60 g of sodium are added. After dissolution of the metal, 100 ml of water are added, and the solvent is substantially removed in vacuo. 300 ml of water are added to the residue, and it is extracted three times with 200 ml of ether. The ethereal phase is dried over sodium sulfate, concentrated, and distilled in vacuo.

Yield 93 g (abt. 90% of th.) b.p. 69°–72° C. at 8 mm Hg.

EXAMPLE 3

Spiro[4.5]-2-aza-decane-3-carbonitrile 80.2 g of aminomethyl-di-(ethyloxy)ethyl-cyclohexane are stirred for about 1 hour under inert gas ($N_2$ or Ar) in a mixture of 300 ml of ethanol and 300 ml of 1N hydrochloric acid. After complete cleavage of the starting product, the solution is cooled to 0° C., and rapidly adjusted to pH 5 by adding 2N sodium hydroxide solution. 300 ml of glacial acetic acid (pH about 3) are added immediately thereafter, the batch is cooled to −10° C., and 17.5 g of sodium cyanide are added. The reaction vessel is closed and maintained for 5 hours at room temperature. By thin-layer chromatography control (system ethyl acetate/petroleum ether 2:1) the completed reaction is stated (Schiff's base Rf=0.6–0.7; aminonitrile Rf=0.28), and the reaction solution is concentrated to dryness. The crude aminonitrile is then processed according to Example 4 or 5.

EXAMPLE 4

Spiro[4.5]-2-aza-decane-3-carboxylic acid 250 ml of 4N hydrochloric acid are added to half of the aminonitrile obtained in Example 3, and the whole is refluxed for 4 hours. Traces of escaping hydrocyanic acid are destroyed in suitable manner (freezing-out, absorption in basic iron(II) salt solution). The solution is neutralized, dried, and extracted several times with n-butanol. The evaporation residue of the organic phase is (a) crystallized from chloroform/diisopropyl ether in order to obtain the hydrochloride, and if necessary reprecipitated from a mixture with ethanol, or (b) purified by stirring with ion exchanger (for example IR 45 Amberlite ®) in aqueous solution, and the zwitter ion is crystallized from ethanol/ether after the water has been removed.

Yield according to (a): 31–32 g (82%)
m.p. 205° C. (dec.) hydrochloride

EXAMPLE 5

Spiro[4.5]-2-aza-decane-3-carboxylic acid benzyl ester-hydrochloride

Half of the aminonitrile obtained according to Example 3 is absorbed in 70 ml of benzyl alcohol. At room temperature, a HCl gas current is slowly passed through the solution for 5 minutes, the batch is maintained for 2 to 3 hours at room temperature, and then well concentrated in vacuo. Aqueous bicarbonate solution is subsequently added until pH 8.5 has adjusted, and the benzyl ester is extracted with ethyl acetate. The organic phase is dried, combined with an equivalent amount of ethereal hydrochloric acid, and concentrated. The residue is crystallized from diisopropyl ether, and it can be recrystallized from methylene chloride/diisopropyl ether.

Yield: 43 g (abt. 80%)
m.p. 145° C. (decomposition)

What is claimed is:

1. Compound of the formula I

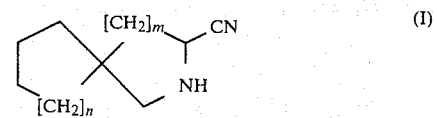

in which m is an integer of from 1 to 3 and n is an integer of from 1 to 4.

2. A compound of the formula I as claimed in claim 1, wherein m is 1.

* * * * *